United States Patent [19]
Lee

[11] Patent Number: 5,125,904
[45] Date of Patent: Jun. 30, 1992

[54] SPLITTABLE HEMOSTATIC VALVE AND SHEATH AND THE METHOD FOR USING THE SAME

[76] Inventor: Hongpyo H. Lee, 9 Amber Sky Dr., Rancho Palos Verdes, Calif. 90274

[21] Appl. No.: 727,191

[22] Filed: Jul. 9, 1991

[51] Int. Cl.[5] .............................................. A61H 5/178
[52] U.S. Cl. ...................................... 604/164; 604/161
[58] Field of Search ............... 604/167, 169, 160, 161, 604/256, 164, 200, 201, 202, 205, 236, 905, 166, 165, 264; 251/149.1; 137/843, 844, 845, 849

[56] References Cited

U.S. PATENT DOCUMENTS

| | | | |
|---|---|---|---|
| 3,653,388 | 4/1972 | Tenckhoff | 604/161 |
| 4,596,559 | 6/1986 | Fleischhacker | 604/161 |
| 4,772,266 | 9/1988 | Groshong | 604/164 |
| 4,921,479 | 5/1990 | Grayzel | 604/164 |
| 4,960,412 | 10/1990 | Fink | 604/167 |

FOREIGN PATENT DOCUMENTS 3140915  5/1982  Fed. Rep. of Germany ...... 604/161

*Primary Examiner*—Cary E. O'Connor
*Attorney, Agent, or Firm*—Daniel L. Dawes

[57] ABSTRACT

A splittable hemostatic valve and introducer sheath is provided for introductions of leads or catheters through the valve and sheath combination into a vein or artery. Because of the hemostatic valve, this sheath can remain in the vein throughout the operation with the advantage of free lead exchange possibility and easier lead manipulation, especially in dual lead insertions, without bleeding, risk of air embolism or repeated sheath insertion related trauma for lead exchange. A side arm to the hemostatic valve cage provides continuous fluid drip in order to prevent clot formation in the lumen of the sheath. At the point in the operation where the introducer sheath and hemostatic valve must be removed from the lead or catheter, which must remain implanted, means are employed to split or separate the introducer sheath and valve apart so that the sheath and valve are removed from the implanted lead or catheter without the necessity of sliding either the sheath or valve over the free end of the lead or catheter. In this manner, any termination which may be provided on the free end of the lead or catheter, such as a terminal for connection to a pacemaker, will not interfere with the optimal use of the introducer sheath and hemostatic valve.

19 Claims, 1 Drawing Sheet

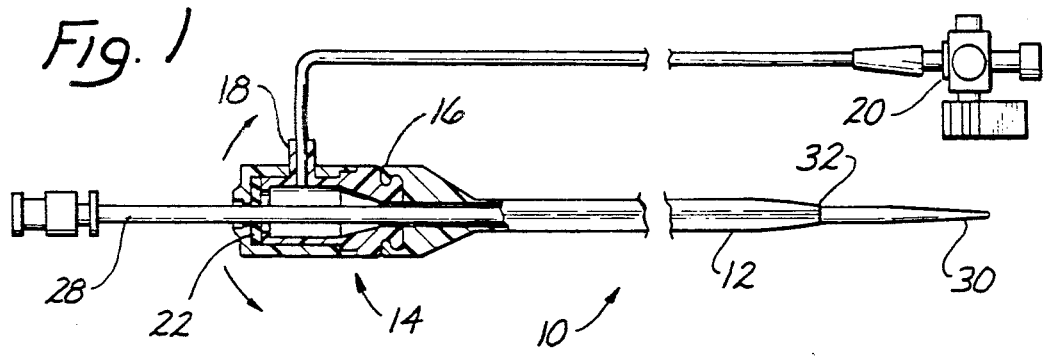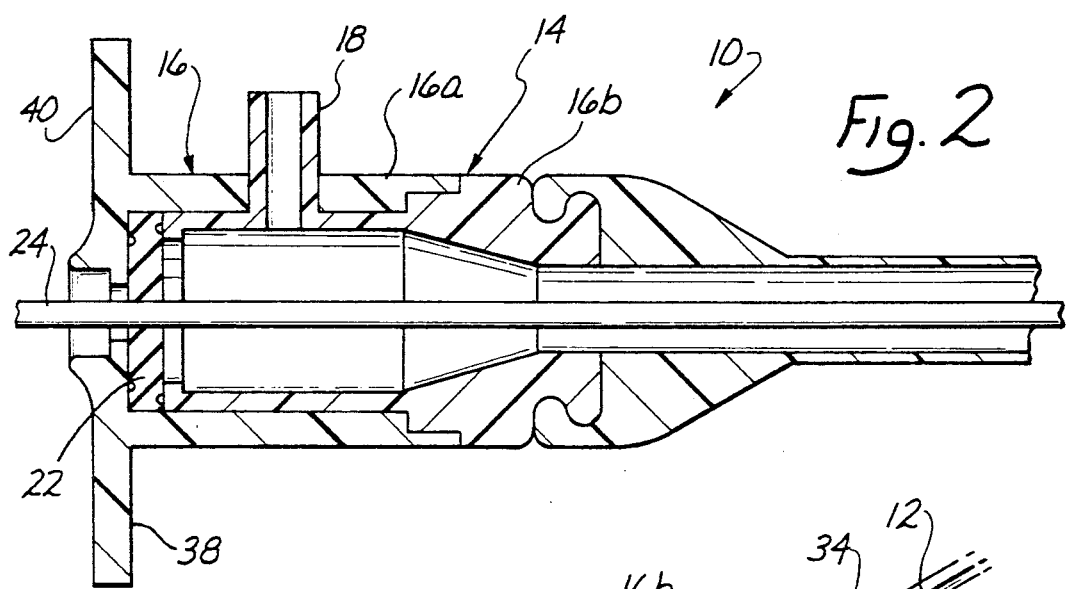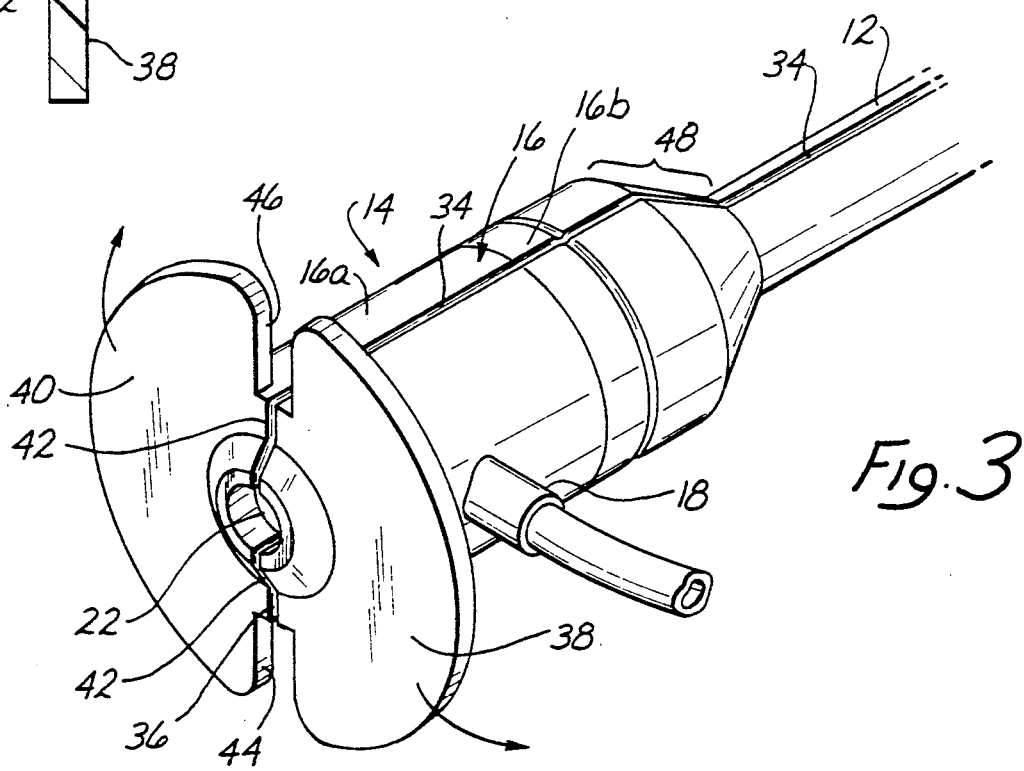

SPLITTABLE HEMOSTATIC VALVE AND SHEATH AND THE METHOD FOR USING THE SAME

BACKGROUND OF THE INVENTION

1. Field of the Invention

The invention relates to the field of pacemaker leads and catheters and methods for insertion of the same, and in particular to leads used in veins such as in connection with pacemaker procedures such as pacemaker lead insertion.

2. Description of the Prior Art

There are many medical procedures which require a puncture and catheterization of an artery or vein for various purposes.

In the prior art process of percutaneous puncture, a guidewire is introduced into the vessel through a hollow needle. The needle is withdrawn leaving the guidewire in the vessel. A TEFLON dilator and venous sheath assembly are then advanced in a rotary motion over the guidewire into the vessel. The TEFLON dilator and the guidewire are then removed leaving the flexible sheath in the vessel. At this point, various types of catheters or leads are inserted using the sheath as a conduit to avoid tearing or further trauma to the vessel wall.

In the case where a pacemaker lead must be permanently inserted into the patient, the pacemaker is subcutaneously implanted in the patient and the lead, which extends from the pacemaker into the heart chamber, remains permanently disposed through the vessel wall and in the vessel lumen. A sheath is nevertheless used in order to guide insertion of the lead into vein lumen, but must be removed leaving the lead in place. However, the sheath cannot simply, in all cases, be slipped over the the exterior end of the pacemaker lead which may be provided with a special termination for connection to the pacemaker.

In this case, the prior art has devised a number of splittable or peel away sheaths. The sheath is scored so that it is withdrawn by splitting or peeling it off from the pacemaker catheter. See Phillip O. Littleford, et al, "The American Journal of Cardiology," Vol. 43,pp.980-982 (May 1979); Littleford, "Apparatus and Method for Inserting an Electrode," U.S. Pat. No. 4,166,469 (1979); Littleford, "Method for Inserting Pacemaker Electrodes and the Like," U.S. Pat. No. 4,243,050 (1981) and Littleford, "Split Sleeve Introducers for Pacemaker Electrodes and the Like," U.S. Pat. No. 4,345,606 (1982); Osborne, "Tear Apart Cannula," U.S. Pat. No. Re. 31,855 (1985), a reissue of U.S. Pat. No. 4,306,562 (1981); Boarini et al., "Peelable Catheter with Securing Ring and Suture Sleeve," U.S. Pat. No. 4,411,654 (1983); Moorehead, "Medical Layered Peel Away Sheath and Methods," U.S. Pat. No. 4,983,168 (1991). A splittable cannula is also taught by Kousai et al., "Medical Tool Introduction Cannula and Method of Manufacturing the Same," U.S. Pat. No. 4,883,468 (1989).

However, in each of these prior art sheath assemblies, once the sheath has been inserted the sheath provides a passage for the free flow of blood. In practice a significant amount of bleeding may occur at the operation site, which requires constant mopping and cleaning. The amount of loss of blood during an operation may begin to have a negative impact upon the patient.

Secondly, in addition to the sheath assembly providing an open passage for the loss of blood, the sheath assembly also provides an open passage for the introduction of air into the vein. The inadvertent introduction of air into the blood system causes air embolism in the patient and its consequent negative effects.

Thirdly, clotting may be formed in the lumen of the sheath if the sheath remains in for a prolonged time, and this may cause embolism to the lung and its consequent negative effects.

Because of the three problems above, the prior art splittable sheath has to be removed as soon as the lead is introduced into the vessel lumen, although it is very desirable to retain the sheath in place throughout operation because the lead can be manipulated much easier without interference from other existing lead or tissue friction and can be exchanged freely without repeated sheath insertion trauma.

When the catheter or lead is introduced in the sheath, a certain amount of blood leakage will occur between the catheter and the sheath walls. The prior art has also devised hemostatic valves which provide a seal around the catheter introduced through the sheath. One such sheath and hemostatic valve is manufactured and marketed by Cordis Corp. of Miami, Fla. as the UNISTASIS valve in the Cordis catheter sheath introducer. Another example is manufactured by Bard of Billerica, Mass. as the 5F HEMAQUET introducer. A hemostatic valve combined with a splittable sheath is also illustrated in Schiff, "Introducer Assembly for Intra-Aortic Balloons and the Like Incorporating a Sliding, Blood-Tight Seal," U.S. Pat. No. 4,473,067 (1984).

However, all the prior art hemostatic valve structures, even when combined with a splittable sheath, such as shown by Schiff, are integral or or rigid units, which do not split and must be removed by sliding along the end of the catheter. In the case of Schiff, the sheath is split in order to appropriately position the balloon catheter. However, after the baloon angioplasty procedure is completed, the entire catheter is removed so that at no point is the hemostatic valve entirely removed from the catheter nor need it be.

What is needed then is some type of sheath and valve system which can be used in connection with our vessel introducers, which introducers can then remain in place without risking undue bleeding, air embolism, or clotting while retaining the advantages of an introducer sheath for free lead exchange and easier lead manipulation.

BRIEF SUMMARY OF THE INVENTION

The invention is a sheath assembly for use with a lead or catheter comprising an introducer sheath, and a hemostatic valve coupled to the introducer sheath. The hemostatic valve and introducer sheath are arranged and configured to permit introduction of at least one lead or catheter therethrough. An element is provided to permit removal of the hemostatic valve and introducer sheath from the catheter disposed therethrough without requiring the introducer sheath and hemostatic valve to be removed from an end of the catheter. A side arm is connected to hemostatic valve cage and provides continuous fluid drip in order to prevent clot formation in the sheath lumen.

As a result, the assembly may safely remain in the vessel lumen throughout the operation without substantial bleeding, risk of air embolism, clotting, or need of repeated sheath insertion for lead exchange.

The element for permitting removal of the hemostatic valve and introducer sheath is a element for splitting the introducer sheath and hemostatic valve away from the lead or catheter is disposed therethrough.

Alternatively, the element for permitting removal of the introducer sheath and the hemostatic valve is a element for peeling away the introducer sheath and hemostatic valve from the lead or catheter disposable therethrough.

In the illustrated embodiment the element for permitting removal of the hemostatic valve and introducer sheath is a score line defined in the hemostatic valve and introducer sheath along which the hemostatic valve and introducer sheath may be separated. The score line comprises a pair of lines defined in the hemostatic valve and introducer sheath. The pair of score lines are diametrically opposed from each other on the hemostatic valve and introducer sheath. The score line is disposed along the longitudinal length of the hemostatic valve and introducer sheath. The score line defined into the introducer sheath is aligned with the score line defined into the hemostatic valve. The introducer sheath and hemostatic valve are integrally formed and the element for permitting removal of the valve and sheath permits removal of the valve and sheath as an integral body from the catheter disposed therethrough.

In another embodiment the introducer sheath and hemostatic valve are separate body portions coupled to each other and the element for permitting removal of the valve and sheath from the lead or catheter allow separate removal of the hemostatic valve and sheath from the lead or catheter.

The hemostatic valve is self sealing. The hemostatic valve and sheath are arranged and configured to allow the insertion therethrough of multiple leads or catheters. The hemostatic valve further comprises an intravenous sidearm assembly. The element for permitting removal of the hemostatic valve and sheath leaves the sidearm assembly intact.

The invention is also characterized as a method for percutaneous sheath lead or catheterization comprising the steps of disposing an introducer sheath and hemostatic valve coupled to the introducer sheath into a body lumen. At least one lead or catheter is disposed through the valve and introducer sheath into the body lumen. The lead or catheter is sealed within the hemostatic valve to prevent bleeding and introduction of air into the body lumen with dispostion of the lead or catheter therein. The hemostatic valve and introducer sheath is removed while leaving the lead or catheter in place within the body lumen without sliding either the introducer sheath or hemostatic valve over an end of the lead or catheter. As a result, implanted leads or catheters may be disposed into the body lumen without bleeding, risk of air embolism, clotting or requiring the end of the lead or catheter to have a structure to permit removal of the sheath and valve thereover.

The step of removing the sheath and lead or catheter comprises the step of splitting the sheath and valve along a longitudinal length of the sheath and valve and disposing the lead or catheter radially through the longitidinal split.

More particularly, the step of splitting the sheath and valve comprises a step of splitting the sheath and valve along a score line by manually tearing the sheath and valve apart along the score line.

The step of tearing the sheath and valve along a score line further comprises tearing the sheath and valve along a pair of longitudinally defined score lines in the sheath and valve. The step of tearing the valve and sheath along a pair of score lines comprises in turn the step of tearing the valve and sheath along diametrically opposing longitudinally defined score lines in the valve and sheath respectively.

The invention is still further characterized as an improvement in an introducer sheath and valve assembly for implantation of pacemaker leads comprising an element for splitting the introducer sheath. The sheath has a longitudinal axis. The element for splitting allows manual separation of the sheath along the longitudinal axis. An other element for separating the hemostatic valve permits removal of the valve from the lead without necessitating removal of the valve over an end of the lead. As a result, the sheath can remain in place throughout the operation with the advantage of free lead exchange and easier lead manipulation without bleeding, air embolism, clotting and repeated sheath related trauma for possible lead exchange.

BRIEF DESCRIPTION OF THE DRAWINGS

FIG. 1 is a partially cutaway side view of a splittable introducer sheath devised according to the invention.

FIG. 2 is an enlargement of the splittable valve portion shown in FIG. 1 wherein a lead or catheter has been disposed through the valve.

FIG. 3 is a rear prospective view of the valve and sheath combinations of FIGS. 1 and 2 showing an embodiment of diametric longitudinal score lines.

The invention and its various embodiments may now be understood by turning to the following detailed description.

DETAILED DESCRIPTION OF THE PREFERRED EMBODIMENTS

An improved hemostatic valve and introducer sheath is provided for introductions of leads or catheters through the valve and sheath combination into a vessel or artery. At the point in the operation where the introducer sheath and hemostatic valve must be removed from the lead or catheter, which must remain implanted, means are employed to split or separate the introducer sheath and valve apart so that the sheath and valve are removed from the implanted lead or catheter without the necessity of sliding either the sheath or valve over the free end of the lead or catheter. In this manner, any termination which may be provided on the free end of the lead or catheter, such as a terminal for connection to a pacemaker, will not interfere with the optimal use of the introducer sheath and hemostatic valve.

A splittable introducer sheath and valve assembly, generally noted by reference numeral 10 in FIG. 1, is depicted in partially cutaway side view. Valve and sheath assembly 10 comprise a splittable sheath 12 connected, coupled or extending from a splittable hemostatic valve assembly 14. Valve assembly 14 in turn is comprised of a valve body 16, an intravenous sidearm 18 with a sidearm 18 are largely inconsequential to the present invention and therefore will not be further described except insofar as necessary to illustrate the invention. Hemostatic valve assembly 14 is shown in FIG. 1 in cutaway view exposing the interior of valve 16 which includes a valve membrane 22. The details of valve assembly 14 again are not critical to an understanding of the invention, but in the preferred embodiment, valve membrane 22 is a self-healing membrane through which a lead or catheter may be introduced without leakage between membrane 22 and leads or lead 24 such as shown in the partially cutaway view of FIG. 2 depicted in expanded scale. Valve body 16 in the illustrated embodiment is comprised of two sections 16a and b which are bonded together after assembly.

In the depiction of FIG. 1, a conventional dilator 28 is shown as disposed through valve assembly 14 and sheath 12 having a tapered tip 30 extending from the distal end 32 of sheath 12. As in the conventional methodology described above in connection with percutaneous sheath lead or catheterization, the artery or vessel is punctured with a needle into which a guidewire is placed. The needle removed and then dilator and sheath assembly 12 advanced on the guidewire into the vessel. The guidewire will extend through valve assembly 14 and be sealed by means of membrane 22. The guidewires and TEFLON dilator are then removed leaving the flexible sheath assembly 10 in place. However virtually no bleeding occurs since the entire assembly is sealed by self-healing membrane 22. At this point one or more leads or catheters as suggested in FIG. 2 can be introduced, removed and reintroduced and manipulated without any significant possibility of bleeding, clotting, risk of air embolism or repeated sheath insertion related trauma since once inserted sheath assembly 10 is in place regardless of the number of leads or catheters inserted and removed throughout the operation.

In addition, since sealing of lead or catheter 24 is effectuated by membrane 22 of valve assembly 14, valve body 16 and at least a portion of sheath 12 may be made larger than normal to allow a more loose fit between the interior surfaces of introducer sheath assembly 10 and lead or catheter 24, since blood sealing between the lead or catheter and sheath 12 is not required. This allows leads or catheters 24 and 26 to be introduced and removed from introducer sheath assembly 10 with less friction or interference with assembly 10 and with each other. Therefore the lead can be manipulated much easier.

The detailed construction of sheath 12 and valve assembly 14 as previously implied is not critical to the invention, at least to the extent of whether sheath 12 and valve assembly 10 must be separate or integral parts or how they may be connected with each other. Therefore, it must be expressly understood that valve assembly 14 and sheath 12 may be fabricated according to any structure or out of any material now known to the art or later devised without departing from the spirit and scope of the invention. For example, sheath 12 may be integrally molded or cast with valve assembly, may be adhesively affixed thereto, may be compression fitted, slip fit, threaded, or connected in any manner desired to valve assembly 14 consistent with the teachings of the present invention.

FIG. 3 illustrates in enlarged scale a rear perspective view of introducer sheath assembly 10. According to the invention, both valve assembly 14 and sheath 12 are splittable or have a peel away construction. Again, the detailed nature by which such splittable structure is implemented or how peel-away feature is realized is not critical to the invention. Any method now known or later devised by which such sheaths 12 and valve assemblies 14 may be split or separated may be employed and are contemplated as being within the scope of the invention.

In the illustrated embodiment, sheath 12 and valve assembly 14 are shown as integrally fabricated and having a pair of longitudinal score lines 34 and 36 defined along their axial length. Score lines 34 and 36 are shown as being diametrically opposed from each other across the cross section of introducer sheath 10. Intravenous sidearm 18 is depicted in FIG. 3 as being disposed between score lines 34 and 36 interlying surface between them. Score lines 34 and 36 are shown as having a V-shaped cross section but have such a shape and depth as to permit the entire length of introducer sheath 10 to be manually separated. It is contemplated that at the end of the operation the physician will grasp opposing flange portions 38 and 40 to peel them apart while pulling out the sheath and holding the lead. This will cause valve body 16 to tear along a section line depicted by dotted lines 42 through the body of valve assembly 14. Both body portions 16a and b may be scored to facilitate this tearing. In addition the bonding of the body portions 16a and 16b assists in tearing the inner body portion as the outer body portion is being torn along its corresponding tear line. The portions become through the bonding as a single body and the fracture or tear propagates from the outer body portion through the inner body portion. Membrane 22 has a weak line or score line and can easily be removed from the lead.

In the illustrated embodiment flanges 38 and 40 are formed in two halves having diametrically opposing slots 44 and 46 aligned with score lines 34 and 36 defined into valve body 16. However, it is entirely possible that score lines 34 and 36 will be continued through flanges 38 and 40 to provide deep scores instead of open slots 44 and 46.

In any case, valve body 16 is peeled apart with separation continuing through any transition portion 48 between valve body 16 and sheath 12 and on along the longitudinal length of sheath 12. Sheath 12 is then removed and peeled followed by additional removal of sheath 12 from the puncture site and peeling of the removed portions until the entire valve and introducer sheath assembly 10 of FIG. 1 has been split and removed from the lead or catheter, which is then permanently implanted into the puncture site and with which the surrounding tissue makes a blood tight seal.

Many alterations and modifications may be made by those having ordinary skill in the art without departing from the spirit and scope of the invention. Therefore, it must be expressly understood that the illustrated embodiment has been shown only for the purposes of example and should not be taken as limiting the invention which is defined by the following claims. The following claims are thus to be read as not only literally including what is set forth by the claims but also to include all equivalent elements for performing substantially the same function in substantially the same way to obtain substantially the same result even though not identical in other respects to what is shown and described in the above illustration.

I claim:

1. An sheath assembly for use with a lead or catheter comprising:
    an introducer sheath;
    a hemostatic valve coupled to said introducer sheath, said hemostatic valve and introducer sheath being arranged and configured to permit introduction of at least one lead or catheter therethrough;
    means for permitting removal of said hemostatic valve and introducer sheath from said lead or catheter disposed therethrough without requiring said introducer sheath and hemostatic valve to be removed from an end of said lead or catheter, whereby said assembly may remain in a vein throughout an operation with the advantage of free lead exchange and easier lead manipulation without substantial bleeding, risk of air embolism, clotting or repeated sheath insertion related trauma from lead exchange.

2. The assembly of claim 1 wherein said means for permitting removal of said hemostatic valve and introducer sheath is a means for splitting said introducer sheath and hemostatic valve away from said lead or catheter which is disposed therethrough.

3. The assembly of claim 1 wherein said means for permitting removal of said introducer sheath and said hemostatic valve is a means for peeling away said introducer sheath and hemostatic valve from said lead or catheter disposable therethrough.

4. The assembly of claim 1 wherein said means for permitting removal of said hemostatic valve and introducer sheath is a score line defined in said hemostatic valve and introducer sheath along which said hemostatic valve and introducer sheath may be separated.

5. The assembly of claim 4 wherein said score line comprises a pair of score lines defined in said hemostatic valve and introducer sheath.

6. The assembly of claim 5 wherein said pair of score lines are diametrically opposed from each other on said hemostatic valve and introducer sheath.

7. The assembly of claim 4 wherein said score line is disposed along the longitudinal length of said hemostatic valve and introducer sheath.

8. The assembly of claim 7 wherein said score line defined into said introducer sheath is aligned with said score line defined into said hemostatic valve.

9. The assembly of claim 1 wherein said introducer sheath and hemostatic valve are integrally formed and wherein said means for permitting removal of said valve and sheath permits removal of said valve and sheath as an integral body from said lead or catheter disposable therethrough.

10. The assembly of claim 1 wherein said hemostatic valve is self sealing.

11. The assembly of claim 1 wherein said hemostatic valve and sheath are arranged and configured to allow the insertion therethrough of multiple leads or catheters.

12. A sheath assembly for use with a lead or catheter comprising:

an introducer sheath;

a hemostatic valve coupled to said introducer sheath, said hemostatic valve and introducer sheath being arranged and configured to permit introduction of at least one lead or catheter therethrough;

means for permitting removal of said hemostatic valve and introducer sheath from said lead or catheter disposed therethrough without requiring said introducer sheath and hemostatic valve to be removed from an end of said lead or catheter, wherein said introducer sheath and hemostatic valve are separate body portions coupled to each other and wherein said means for permitting removal of said valve and sheath from said lead or catheter disposable therethrough allow separate removal of said hemostatic valve and sheath from said lead or catheter, whereby said assembly may remain in a vein throughout an operation with the advantage of free lead exchange and easier lead manipulation without substantial bleeding, risk of air embolism, clotting or repeated sheath insertion related trauma from lead exchange.

13. A method of percutaneous sheath lead or catheterization comprising the steps of:

disposing an introducer sheath and hemostatic valve coupled to said introducer sheath in a body lumen;

disposing at least one lead or catheter through said valve and introducer sheath into said body lumen;

sealing said lead or catheter within said hemostatic valve to prevent bleeding and introduction of air into said body lumen with disposition of said lead or catheter therein;

continuously introducing fluid through a sidearm disposed in said hemostatic valve downstream from said valve to continuously flush said introducer sheath to prevent coagulation in said introducer sheath; and removing said hemostatic valve and introducer sheath while leaving said lead or catheter in place within said body lumen without sliding either said introducer sheath or hemostatic valve over an end of said lead or catheter, whereby implanted leads or catheters may be disposed into said body lumen without bleeding, risk of air embolism, clotting or repeated sheath insertion related trauma for lead exchange or requiring said end of said lead or catheter to have a structure to permit removal of said sheath and valve thereover.

14. The method of claim 13 where said step of removing said sheath and lead or catheter comprises the step of splitting said sheath and valve along a longitudinal length of said sheath and valve and disposing said lead or catheter radially through said longitudinal split.

15. The method of claim 14 where said step of splitting said sheath and valve comprises a step of splitting said sheath and valve along a score line by manually tearing said sheath and valve apart along said score line.

16. The method of claim 15 where said step of tearing said sheath and valve along a score line further comprises tearing said sheath and valve along a pair of longitudinally defined score lines in said sheath and valve.

17. The method of claim 16 where said step of tearing said valve and sheath along a pair of score lines comprises the step of tearing said valve and sheath along diametrically opposing longitudinally defined score lines in said valve and sheath respectively.

18. An improvement in an introducer sheath and valve assembly for implantation of pacemaker leads comprising:

means for splitting said introducer sheath, said sheath having a longitudinal axis, said means for splitting allowing manual separation of said sheath along said longitudinal axis; and means for separating said valve assembly separately from splitting of said sheath to permit removal of a lead or catheter disposed through said valve from said valve without necessitating removal of said valve over an end of said lead or catheter, whereby bleeding, risk of air embolism, clotting and repeated sheath insertion related trauma from lead exchange is substantially avoided.

19. An improvement in a hemostatic valve for use with a lead or catheter and a splittable an introducer sheath, said hemostatic valve coupled to said introducer sheath, said hemostatic valve and introducer sheath being arranged and configured to permit introduction of at least one lead or catheter therethrough, said improvement comprising means for permitting removal of said hemostatic valve from said lead or catheter disposed therethrough without requiring said introducer sheath and hemostatic valve to be removed from an end of said lead or catheter, wherein said introducer sheath and hemostatic valve are separate body portions coupleable to each other and wherein said means for permitting removal of said valve and sheath from said lead or catheter disposable therethrough allow separate removal of said hemostatic valve and sheath from said lead or catheter, whereby said assembly may remain in a vein throughout an operation with the advantage of free lead exchange and easier lead manipulation without substantial bleeding, risk of air embolism, clotting or repeated sheath insertion related trauma from lead exchange.

* * * * *

UNITED STATES PATENT AND TRADEMARK OFFICE
CERTIFICATE OF CORRECTION

PATENT NO. : 5,125,904
DATED : June 30, 1992
INVENTOR(S) : Hongpyo H. Lee

It is certified that error appears in the above-identified patent and that said Letters Patent is hereby corrected as shown below:

At column 4, line 60, after "sidearm" add of valve 20. The details of the design of sidearm valve 20 and to a certain extent sidearm Signed and Sealed this Thirtieth Day of January, 1996

Attest:

BRUCE LEHMAN

Attesting Officer

Commissioner of Patents and Trademarks

REEXAMINATION CERTIFICATE (3059th)

United States Patent [19]
Lee

[11] B1 5,125,904
[45] Certificate Issued Nov. 19, 1996

[54] SPLITTABLE HEMOSTATIC VALVE SHEATH AND THE METHOD FOR USING THE SAME

[75] Inventor: Hongpyo H. Lee, Rancho Palos Verdes, Calif.

[73] Assignee: HL Medical Inventions, Inc., Rancho Palo Verdes, Calif.

Reexamination Request:
No. 90/003,862, Jun. 19, 1995

Reexamination Certificate for:
Patent No.: 5,125,904
Issued: Jun. 30, 1992
Appl. No.: 727,191
Filed: Jul. 9, 1991

Certificate of Correction issued Jan. 30, 1996.

[51] Int. Cl.$^6$ .................................................. A61H 5/178
[52] U.S. Cl. ................................... 604/164; 604/161
[58] Field of Search ................................... 604/160, 161, 604/164

[56] References Cited

U.S. PATENT DOCUMENTS

| | | | |
|---|---|---|---|
| 4,596,559 | 6/1986 | Fleischhacker | 604/161 |
| 4,747,833 | 5/1988 | Kousai et al. | 604/161 |
| 4,772,266 | 9/1988 | Groshong | 604/164 |
| 4,983,168 | 1/1991 | Moorehead | 604/161 |

FOREIGN PATENT DOCUMENTS

| | | |
|---|---|---|
| 226397 | 6/1987 | European Pat. Off. . |
| 0631793 | 1/1995 | European Pat. Off. . |
| 3721288 | 6/1989 | Germany . |
| 3834600 | 12/1989 | Germany . |

OTHER PUBLICATIONS

Affidavit of Dr. Jürgen Kaiser, dated 17 Aug. 1994.

*Primary Examiner*—Cary E. O'Connor

[57] ABSTRACT

A splittable hemostatic valve and introducer sheath is provided for introduction of leads or catheters through the valve and sheath combination into a vein or artery. Because of the hemostatic valve, this sheath can remain in the vein throughout the operation with the advantage of free lead exchange possibility and easier lead manipulation, especially in dual lead insertions, without bleeding, risk of air embolism or repeated sheath insertion related trauma for lead exchange. A side arm to the hemostatic valve cage provides continuous fluid drip in order to prevent clot formation in the lumen of the sheath. At the point in the operation where the introducer sheath and hemostatic valve must be removed from the lead or catheter, which must remain implanted, means are employed to split or separate the introducer sheath and valve apart so that the sheath and valve are removed from the implanted lead or catheter without the necessity of sliding either the sheath or valve over the free end of the lead or catheter. In this manner, any termination which may be provided on the free end of the lead or catheter, such as a terminal for connection to a pacemaker, will not interfere with the optimal use of the introducer sheath and hemostatic valve.

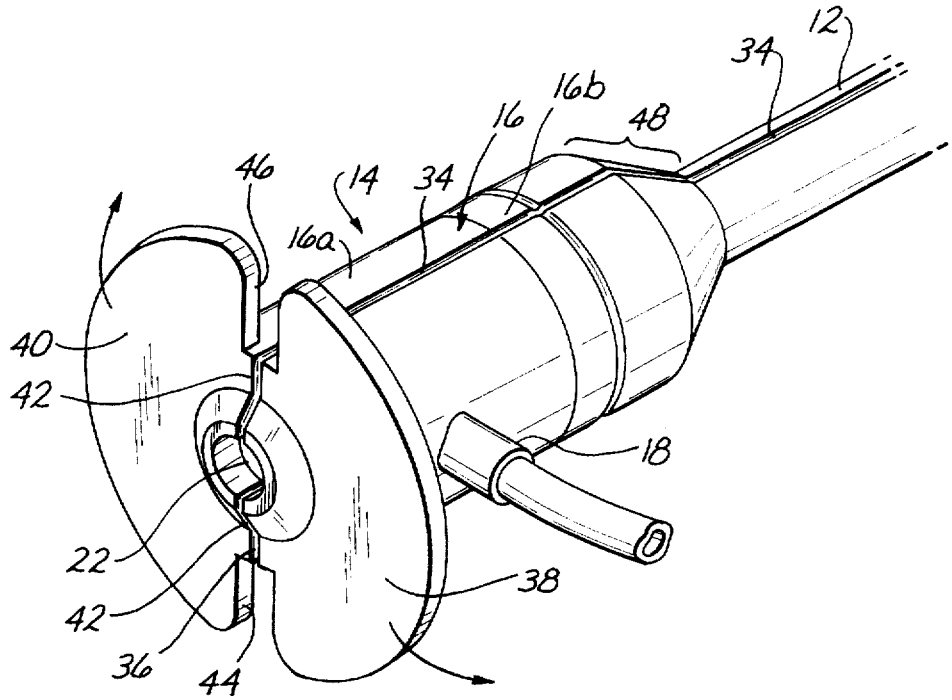

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-8, 10-19 is confirmed.

Claim 9 is determined to be patentable as amended.

New claims 20-34 are added and determined to be patentable.

9. [The assembly of claim 1] *A sheath assembly for use with a lead or catheter* comprising:

an introducer sheath;

a hemostatic valve coupled to said introducer sheath, *said hemostatic valve and introducer sheath being arranged and configured to permit introduction of at least one lead or catheter therethrough;* and means for permitting removal of said hemostatic valve and introducer sheath from said lead or catheter disposed therethrough without requiring said introducer sheath and hemostatic valve to be removed from an end of said lead or catheter, wherein said introducer sheath and hemostatic valve are integrally formed and wherein said means for permitting removal of said valve and sheath permits removal of said valve and sheath as an integral body from said lead or catheter disposable therethrough, whereby said assembly may remain in a vein throughout an operation with the advantage of free lead exchange and easier lead manipulation without substantial bleeding, risk of air embolism, clotting or repeated sheath insertion related to trauma from lead exchange.

*20. An assembly for use with a guidewire for vascular implantation of a lead or catheter, said guidewire being disposed into said vascular system through a hollow needle, said needle for invasively entering said vascular system and characterized by an inner diameter, said assembly comprising:*

*an introducer sheath through which said lead or catheter is introduced into a vascular system, said introducer sheath being disposed into said vascular system under the guidance of said guidewire, said guidewire being removed from said vascular system after disposition therein of said introducer sheath;*

*a fluid tight hemostatic valve subassembly coupled to said introducer sheath, said lead or catheter being introduced into said vascular system through said hemostatic valve subassembly and introducer sheath; and*

*means for permitting removal of said hemostatic valve subassembly and introducer sheath from said lead or catheter disposed therethrough without requiring said introducer sheath and hemostatic valve subassembly to be removed from an end of said lead or catheter after said lead or catheter is disposed into said vascular system under the guidance of said introducer sheath,*

*whereby said assembly may remain disposed in part in said vascular system to allow free lead exchange, easier lead manipulation within said introducer sheath, to avoid the risk of air embolism or trauma from repeated lead exchange and sheath insertion.*

*21. The assembly of claim 20 further comprising a dilator, said dilator being disposed through said introducer sheath for supporting said introducer sheath as said introducer sheath is disposed into said vascular system, said dilator and sheath being guided by said guidewire after said needle is removed therefrom, which guidewire has previously been disposed in said vascular system.*

*22. The assembly of claim 21 where said lead or catheter, dilator and sheath have a diameter greater than said inner diameter of said needle.*

*23. An assembly for use with a guidewire for vascular implantation of a lead or catheter, said guidewire being disposed into said vascular system through a hollow needle, said needle for invasively entering said vascular system, said assembly comprising:*

*an introducer sheath through which said lead or catheter is introduced into a vascular system, said introducer sheath being disposed into said vascular system under the guidance of said guidewire, said guidewire being removed from said vascular system after disposition therein of said introducer sheath;*

*a fluid tight hemostatic valve subassembly coupled to said introducer sheath, said lead or catheter being introduced into said vascular system through said hemostatic valve subassembly and introducer sheath; and*

*means for permitting removal of said hemostatic valve subassembly and introducer sheath from said lead or catheter disposed therethrough without requiring said introducer sheath and hemostatic valve subassembly to be removed from an end of said lead or catheter after said lead or catheter is disposed into said vascular system under the guidance of said introducer sheath, wherein said hemostatic valve subassembly comprises membrane means for providing a fluid tight seal with said lead or catheter within said hemostatic valve subassembly to prevent the flow of fluid past said membrane means in either direction within said hemostatic valve subassembly, and a peel-away valve housing for providing a fluid tight enclosure around said membrane means,*

*whereby said assembly may remain disposed in part in said vascular system to allow free lead exchange, easier lead manipulation within said introducer sheath, to avoid the risk of air embolism or trauma from repeated lead exchange and sheath insertion.*

*24. The assembly of claim 23 wherein said membrane means can be peeled away from said lead or catheter.*

*25. The assembly of claim 24 wherein said membrane means is peeled away simultaneously with said peel-away valve housing.*

*26. The assembly of claim 24 wherein said membrane means is peeled away separately from said peel-away valve housing.*

*27. An assembly for vascular implantation of a lead or catheter, into a vascular system through a hollow needle, said needle for invasively entering said vascular system and characterized by an inner diameter, said assembly comprising:*

*an introducer sheath through which said lead or catheter is introduced into said vascular system;*

*a fluid tight hemostatic valve assembly coupled to said introducer sheath, said lead or catheter being intro-* duced into said vascular system through said hemostatic valve subassembly and introducer sheath; and means for permitting removal of said hemostatic valve subassembly and introducer sheath from said lead or catheter disposed therethrough by tearing said hemostatic valve and introducer sheath apart without causing blood splattering or blood aerosol dispersal.

28. The assembly of claim 27 further comprising a dilator, said dilator being disposed through said introducer sheath for supporting said introducer sheath as said introducer sheath is disposed into said vascular system.

29. The assembly of claim 27 where said lead or catheter, dilator and sheath have a diameter greater than said inner diameter of said needle.

30. An assembly for vascular implantation of a lead or catheter, into a vascular system through a hollow needle, said needle for invasively entering said vascular system, said assembly comprising:

an introducer sheath through which said lead or catheter is introduced into said vascular system;

a fluid tight hemostatic valve subassembly coupled to said introducer sheath, said lead or catheter being introduced into said vascular system through said hemostatic valve subassembly and introducer sheath; and means for permitting removal of said hemostatic valve subassembly and introducer sheath from said lead or catheter disposed therethrough by tearing said hemostatic valve and introducer sheath apart without causing blood splattering or blood aerosol dispersal, wherein said hemostatic valve subassembly comprises membrane means for providing a fluid tight seal with said lead or catheter within said hemostatic valve subassembly to prevent the flow of fluid past said membrane means in either direction within said hemostatic valve subassembly, and a peel-away valve housing for providing a fluid tight enclosure around said membrane means.

31. The assembly of claim 30 wherein said membrane means can be peeled away from said lead or catheter.

32. The assembly of claim 31 wherein said membrane means is peeled away simultaneously with said peel-away valve housing.

33. The assembly of claim 31 wherein said membrane means is peeled away separately from said peel-away valve housing.

34. An assembly for use with a guidewire for vascular implantation of a lead or catheter, said guidewire being disposed into said vascular system through a hollow needle, said needle for invasively entering said vascular system, said assembly comprising:

an introducer sheath through which said lead or catheter is introduced into a vascular system, said introducer sheath being disposed into said vascular system under the guidance of said guidewire, said guidewire being removed from said vascular system after disposition therein of said introducer sheath;

a fluid tight hemostatic valve subassembly coupled to said introducer sheath, said lead or catheter being introduced into said vascular system through said hemostatic valve subassembly and introducer sheath; and means for permitting removal of said hemostatic valve subassembly and introducer sheath from said lead or catheter disposed therethrough without requiring said introducer sheath and hemostatic valve subassembly to be removed from an end of said lead or catheter after said lead or catheter is disposed into said vascular system under the guidance of said introducer sheath, wherein said hemostatic valve subassembly comprises a valve means for providing a fluid tight seal with said lead or catheter within said hemostatic valve subassembly to prevent the flow of fluid past said valve means in either direction within said hemostatic valve subassembly, and a peel-away valve housing for providing a fluid tight enclosure around said valve means, whereby said assembly may remain disposed in part in said vascular system to allow free lead exchange, easier lead manipulation within said introducer sheath, to avoid the risk of air embolism or trauma from repeated lead exchange and sheath insertion.

* * * * *